United States Patent
English et al.

(10) Patent No.: US 12,017,081 B2
(45) Date of Patent: Jun. 25, 2024

(54) IMPLANTABLE MEDICAL DEVICE INCLUDING ELECTRODES FORMED THEREIN

(71) Applicant: Cardiac Pacemakers, Inc., St. Paul, MN (US)

(72) Inventors: James Michael English, Cahir (IE); Jean M. Bobgan, Maple Grove, MN (US); Keith R. Maile, New Brighton, MN (US); Ron A. Balczewski, Bloomington, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 296 days.

(21) Appl. No.: 17/175,063

(22) Filed: Feb. 12, 2021

(65) Prior Publication Data
US 2021/0252295 A1    Aug. 19, 2021

Related U.S. Application Data

(60) Provisional application No. 62/976,080, filed on Feb. 13, 2020.

(51) Int. Cl.
*A61N 1/375*    (2006.01)

(52) U.S. Cl.
CPC ....... *A61N 1/37512* (2017.08); *A61N 1/3756* (2013.01)

(58) Field of Classification Search
CPC .............. A61N 1/37512; A61N 1/3756; A61N 1/37229; A61B 2562/125
See application file for complete search history.

(56) References Cited

U.S. PATENT DOCUMENTS

| | | | |
|---|---|---|---|
| 8,150,517 B2 * | 4/2012 | Dal Molin | A61N 1/37512 607/36 |
| 2008/0183225 A1 | 7/2008 | Adamski | |
| 2012/0303105 A1 * | 11/2012 | Askarinya | A61N 1/37512 29/874 |

FOREIGN PATENT DOCUMENTS

| | | |
|---|---|---|
| WO | 02/34332 A1 | 5/2002 |
| WO | 2012/161915 A2 | 11/2012 |

OTHER PUBLICATIONS

International Search Report and Written Opinion for International patent application No. PCT/US2021/017902, filed Feb. 12, 2021, mailed May 27, 2021.

* cited by examiner

*Primary Examiner* — Tammie K Marlen
(74) *Attorney, Agent, or Firm* — Faegre Drinker Biddle & Reath LLP

(57) ABSTRACT

Embodiments of the present disclosure relate to implantable medical devices. According to an exemplary embodiment, a method for forming an electrode on an implantable medical device (IMD), comprises forming a nonconductive body comprising a well having a bottom surface and at least one side surface extending from the bottom surface. The method further comprises forming a conduit through the bottom surface and inserting the nonconductive body into an opening in an external surface of the IMD. The method also comprises depositing conductive material into the well and coupling the conductive material to a circuit of the IMD via the conduit through the bottom surface of the well.

19 Claims, 4 Drawing Sheets

IMPLANTABLE MEDICAL DEVICE INCLUDING ELECTRODES FORMED THEREIN

CROSS REFERENCE TO RELATED APPLICATION

This application claims priority to Provisional Application No. 62/976,080, filed Feb. 13, 2020, which is herein incorporated by reference in its entirety.

TECHNICAL FIELD

Embodiments of the present disclosure relate to medical devices and systems for sensing physiological parameters and/or delivering therapy. More specifically, embodiments of the disclosure relate to devices and methods for forming electrodes with a nonconductive body.

BACKGROUND

Implantable medical devices (IMDs) may be configured to sense physiological parameters and/or provide therapy and may include one or more electrodes for performing aspects of these functions. IMDs may also include antennas for communicating with other devices. Conventionally, devices such as programmers and wands have been used to cause IMDs to take various actions such as for example, marking recordings of physiological parameters, initiating communications with other devices, and the like.

SUMMARY

Exemplary embodiments of the present disclosure include, but are not limited to, the following examples.

In an Example 1, a method for forming an electrode on an implantable medical device (IMD), comprises: forming a nonconductive body comprising a well having a bottom surface and at least one side surface extending from the bottom surface; forming a conduit through the bottom surface; inserting the nonconductive body into an opening in an external surface of the IMD; depositing conductive material into the well; and coupling the conductive material to a circuit of the IMD via the conduit through the bottom surface of the well.

In an Example 2, the method of Example 1, wherein coupling the conductive material to the circuit of the IMD comprises brazing a wire that couples the conductive material to the circuit.

In an Example 3, the method of any one of Examples 1 or 2, wherein the at least one side extends perpendicular from the bottom surface.

In an Example 4, the method of any one of Examples 1-3, further comprising surface-grinding a top of the nonconductive body, the conductive material, or the nonconductive body and the conductive material to remove excess of the nonconductive body, the conductive material, or the nonconductive body and the conductive material.

In an Example 5, the method of any one of Examples 1-4, further comprising laser etching a top of the nonconductive body, the conductive material, or the nonconductive body and the conductive material to remove excess of the nonconductive body, the conductive material, or the nonconductive body and the conductive material.

In an Example 6, the method of any one of Examples 1-5, further comprising applying a mask to the conductive material to remove any excess of the conductive material.

In an Example 7, the method of any one of Examples 1-6, wherein depositing conductive material into the well comprises using photolithography and/or vapor deposition techniques.

In an Example 8, the method of any one of Examples 1-7, wherein the conductive material is titanium nitride (TiN).

In an Example 9, the method of any one of Examples 1-8, wherein the nonconductive body is made of ceramic, glass, or sapphire.

In an Example 10, the method of any one of Examples 1-9, wherein the well is approximately 0.1 to 1 millimeters deep In an Example 11, the method of any one of Examples 1-10, wherein an outer diameter of the nonconductive body is between approximately 1.1 to 1.5 times larger a diameter of the bottom surface.

In an Example 12, an implantable medical device (IMD), comprising: a housing enclosing a power supply, a processing device, and memory; a nonconductive body arranged in an opening of the housing, the nonconductive body comprising a well having a bottom surface and at least one side surface extending from the bottom surface; a conductive material deposited into the well, wherein the conductive material is electrically coupled to the processing device.

In an Example 13, the IMD of Example 12, wherein a top surface of the conductive material is flush with a top surface of the housing, wherein a top surface of the conductive material is flush with a top surface of the nonconductive body, or wherein a top surface of the conductive material is flush with the top surface of the housing and the top surface of the nonconductive body.

In an Example 14, the IMD of any one of Examples 12 or 13, wherein the at least one side extends perpendicular from the bottom surface.

In an Example 15, the IMD of any one of Examples 12 or 13, wherein the nonconductive body is made of ceramic, glass, or sapphire.

In an Example 16, a method for forming an electrode on an implantable medical device (IMD), comprising: forming a nonconductive body comprising a well having a bottom surface and at least one side surface extending from the bottom surface; forming a conduit through the bottom surface; inserting the nonconductive body into an opening in an external surface of the IMD; depositing conductive material into the well; and coupling the conductive material to a circuit of the IMD via the conduit through the bottom surface of the well.

In an Example 17, the method of Example 16, wherein coupling the conductive material to the circuit of the IMD comprises brazing a wire that couples the conductive material to the circuit.

In an Example 18, the method of Example 16, wherein the at least one side extends perpendicular from the bottom surface.

In an Example 19, the method of Example 16, further comprising surface-grinding a top of the nonconductive body, the conductive material, or the nonconductive body and the conductive material to remove excess of the nonconductive body, the conductive material, or the nonconductive body and the conductive material.

In an Example 20, the method of Example 16, further comprising laser cleaning a top of the nonconductive body, the conductive material, or the nonconductive body and the conductive material to remove excess of the nonconductive body, the conductive material, or the nonconductive body and the conductive material.

In an Example 21, the method of Example 16, further comprising applying a mask to the conductive material to remove any excess of the conductive material.

In an Example 22, the method of Example 16, wherein depositing conductive material into the well comprises using photolithography and/or vapor deposition techniques.

In an Example 23, the method of Example 16, wherein the conductive material is titanium nitride (TiN).

In an Example 24, the method of Example 16, wherein the nonconductive body is made of ceramic, glass, or sapphire.

In an Example 25, the method of Example 16, wherein the well is approximately 0.1 to 1 millimeters deep.

In an Example 26, the method of Example 16, wherein an outer diameter of the nonconductive body is between approximately 1.1 to 1.5 times larger a diameter of the bottom surface.

In an Example 27, an implantable medical device (IMD), comprising: a housing enclosing a power supply, a processing device, and memory; a nonconductive body arranged in an opening of the housing, the nonconductive body comprising a well having a bottom surface and at least one side surface extending from the bottom surface; a conductive material deposited into the well, wherein the conductive material is electrically coupled to the processing device.

In an Example 28, the IMD of Example 27, wherein a top surface of the conductive material is flush with a top surface of the housing, wherein a top surface of the conductive material is flush with a top surface of the nonconductive body, or wherein a top surface of the conductive material is flush with the top surface of the housing and the top surface of the nonconductive body.

In an Example 29, the IMD of Example 27, wherein the at least one side extends perpendicular from the bottom surface.

In an Example 30, the IMD of Example 27, wherein the nonconductive body is made of ceramic, glass, or sapphire.

In an Example 31, the IMD of Example 27, wherein the conductive material is titanium nitride (TiN).

In an Example 32, a method for forming an antenna on an implantable medical device (IMD), comprising: forming an elongated nonconductive body; forming a conduit through the nonconductive body; inserting the nonconductive body into an opening in an external surface of the IMD; depositing a conductive material onto the nonconductive body, wherein the conductive material is deposited in a non-linear path; and coupling the conductive material to a circuit of the IMD via the conduit through the nonconductive body.

In an Example 33, the method of Example 32, further comprising surface-grinding or laser etching a top of the nonconductive body, the conductive material, or the nonconductive body and the conductive material to remove excess of the nonconductive body, the conductive material, or the nonconductive body and the conductive material.

In an Example 34, the method of Example 32, wherein the nonconductive body is made of ceramic, glass, or sapphire.

In an Example 35, the method of Example 32, wherein the conductive material is titanium nitride (TiN).

While multiple embodiments are disclosed, still other embodiments of the present disclosure will become apparent to those skilled in the art from the following detailed description, which shows and describes illustrative embodiments of the subject matter disclosed herein. Accordingly, the drawings and detailed description are to be regarded as illustrative in nature and not restrictive.

Figure 1:
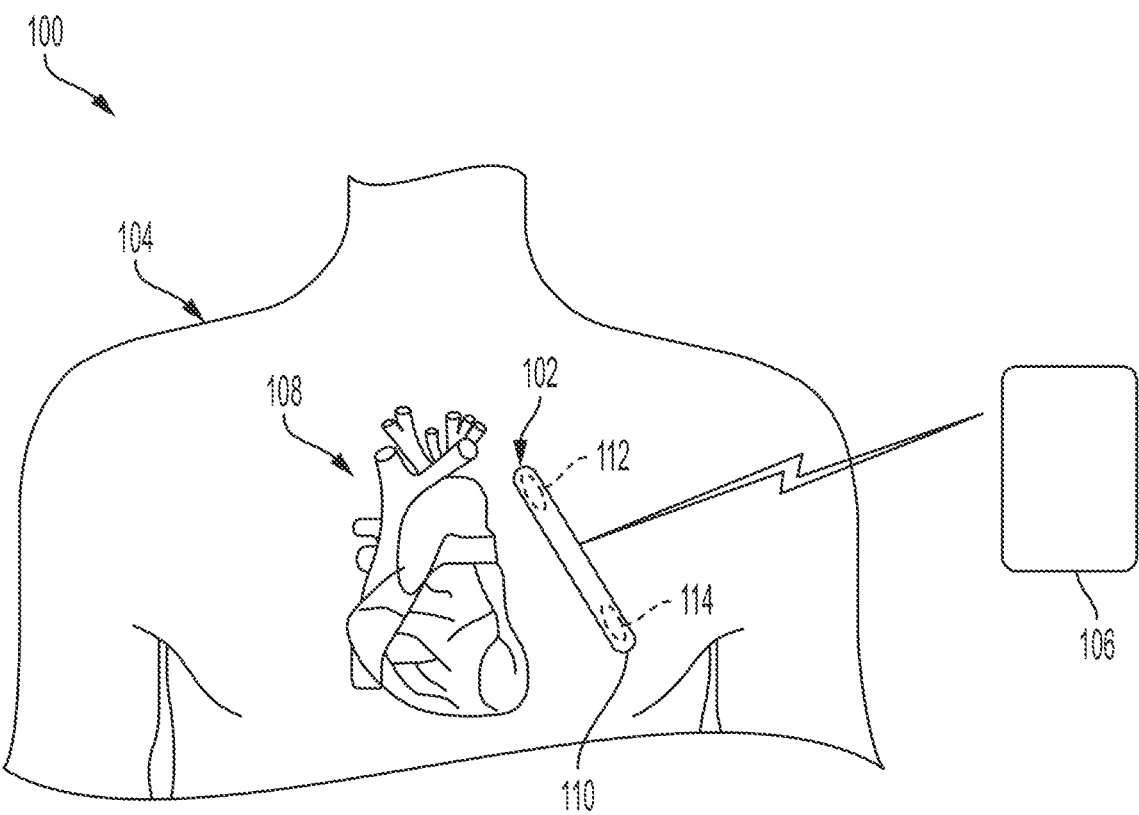
FIG. 1 is a schematic illustration of a system having an implantable medical device (IMD) and a receiving device.

While the subject matter disclosed herein is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the subject matter disclosed herein as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

Implantable medical device (IMD) may be used to sense one or more physiological measurements of a subject. To do so, IMDs often include one or more electrodes, which is attached to an outer surface of the IMDs. The embodiments disclosed herein provide a more efficient and cost-effective way to incorporate electrodes into an IMD.

FIG. 1 is a schematic illustration of a system 100 including an IMD 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac activation signals, heart sounds, blood pressure measurements, oxygen saturations, and/or the like.

In certain instances, the IMD 102 may be configured to monitor physiological parameters that may include one or more signals indicative of a patient's physical activity level and/or metabolic level, such as an acceleration signal. In certain instances, the IMD 102 may be configured to monitor physiological parameters associated with one or more other organs, systems, and/or the like. The IMD 102 may be configured to sense and/or record at regular intervals, continuously, and/or in response to a detected event. In certain instances, such a detected event may be detected by one or more sensors of the IMD 102, another IMD (not shown), an external device (e.g., the receiving device 106), and/or the like.

In addition, the IMD 102 may be configured to detect a variety of physiological signals that may be used in connection with various diagnostic, therapeutic, and/or monitoring implementations. For example, the IMD 102 may include sensors or circuitry for detecting respiratory system signals, cardiac system signals, and/or signals related to patient activity. In certain instances, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient.

As shown, the IMD 102 may include a housing 110 having two electrodes 112 and 114 coupled thereto. According to certain instances, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In certain instances, the IMD 102 may be configured to sense physiological parameters using, e.g., the electrodes 112, 114, and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various instances, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102. In certain instances, the IMD 102 may be a pacemaker, an implantable cardioverter defibrillator (ICD) device, or a cardiac resynchronization therapy (CRT) device. In certain instances, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. The receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

The IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bidirectional communication between the IMD 102 and the receiving device 106. Data and/or control signals may be transmitted between the IMD 102 and the receiving device 106 to coordinate the functions of the IMD 102 and/or the receiving device 106. Patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2:
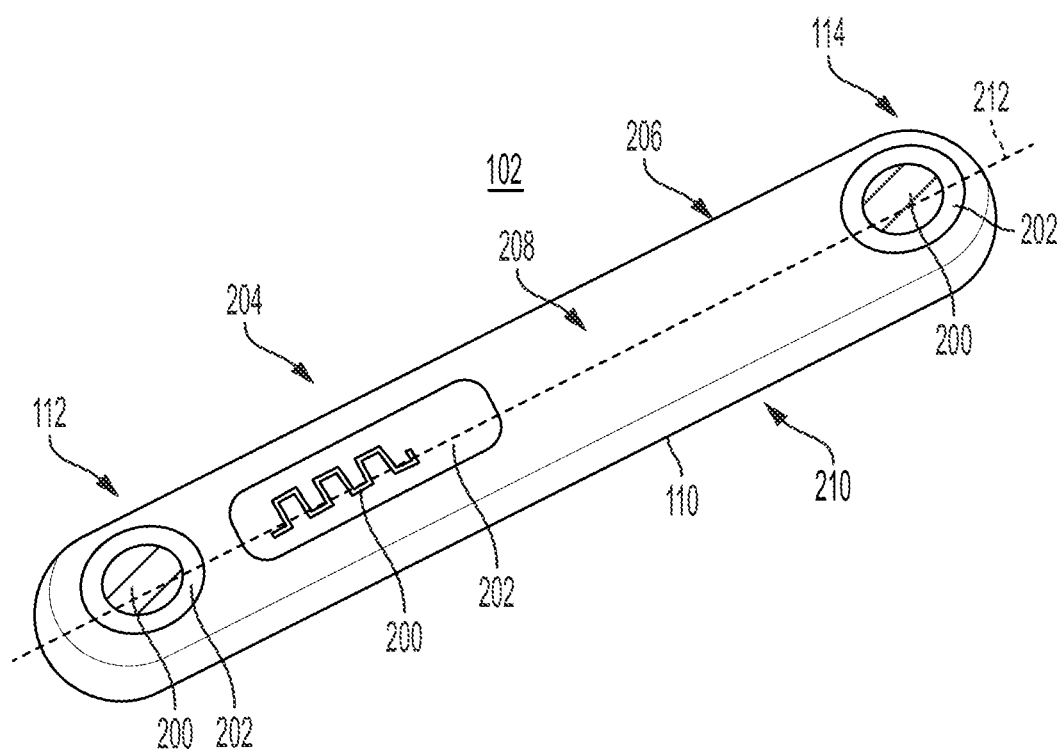
FIG. 2 is a perspective view of an IMD according to an embodiment.

FIG. 2 is a perspective view of the IMD 102 according to an embodiment as disclosed herein. The IMD 102 has the first electrode 112 and the second electrode 114 as well as an antenna 204 embedded in the housing 110. Each of the first electrode 112, the second electrode 114, and the antenna 204 includes a conductive portion 200 that is surrounded by a larger nonconductive portion 202 to prevent the conductive portion 200 from coming into contact with an outer surface 206 of the housing 110, which may be conductive.

In some examples, the electrodes 112 and 114 and the antenna 204 are all located on the same side of the outer surface 206, such as on a frontward facing portion 208 or a rearward facing portion 210 of the outer surface 206. The IMD 102 has a longitudinal axis 212 along which the components of the IMD 102 are positioned. The antenna 204 may be configured for wirelessly communicating data with the receiving device 106. The housing 110 is made of any suitable material such as metal, for example titanium, whereas the nonconductive portions 202 are made of any suitable material with nonconductive or insulating properties such as ceramic substrate, glass, or sapphire, etc. The nonconductive portions 202 may be transparent, translucent, or opaque according to the material used.

Figure 3A:
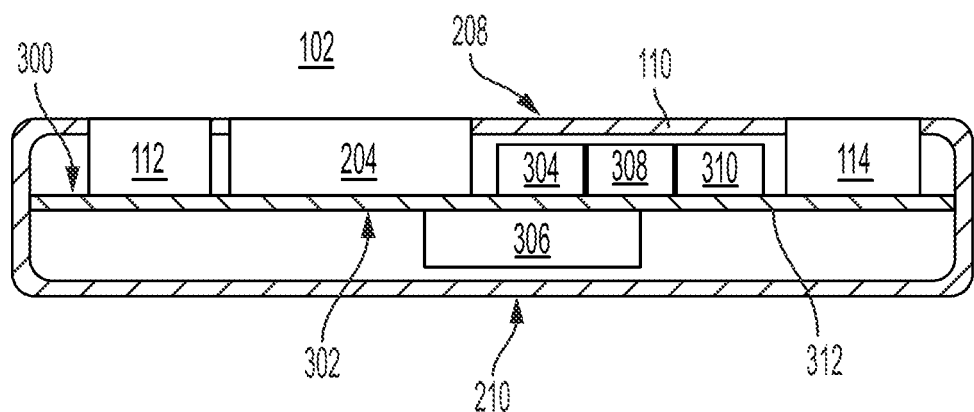
FIG. 3A is a schematic diagram of an IMD according to some embodiments.

FIG. 3A shows an example of the components in IMD 102 according to some embodiments. The housing 110 contains a battery 304, a charging coil 306 for wireless charging of the battery 304 using an external charging device 318, assuming that battery 304 is a rechargeable battery. If the battery 304 is not rechargeable, the charging coil 306 and the external charger 318 can be eliminated. The IMD 102 also includes control circuitry such as a microcontroller 308, and/or one or more Application Specific Integrated Circuit (ASICs) 310, as suitable. ASIC(s) 310 can include current generation circuitry for providing stimulation pulses at one or more of the electrodes 112 and 114 and may also include telemetry modulation and demodulation circuitry for enabling bidirectional wireless communications at the antenna 204, battery charging and protection circuitry couplable to charging coil 306, DC-blocking capacitors in each of the current paths proceeding to the electrodes 112 and 114, etc.

Components within the housing 110 are integrated via a printed circuit board (PCB) 312 which includes electrical traces (not shown) printed on one or more of surfaces 300 and 302 of the PCB 312 to electrically couple the individual components to each other, as suitable. For example, the traces may be used to electrically couple the control circuitry (e.g., microcontroller 308 and ASICs 310) with the electrodes 112, 114 and the antenna 204. The traces are made of any suitable conductive material, such as gold, silver, or platinum alloys, for example.

Figure 3B:
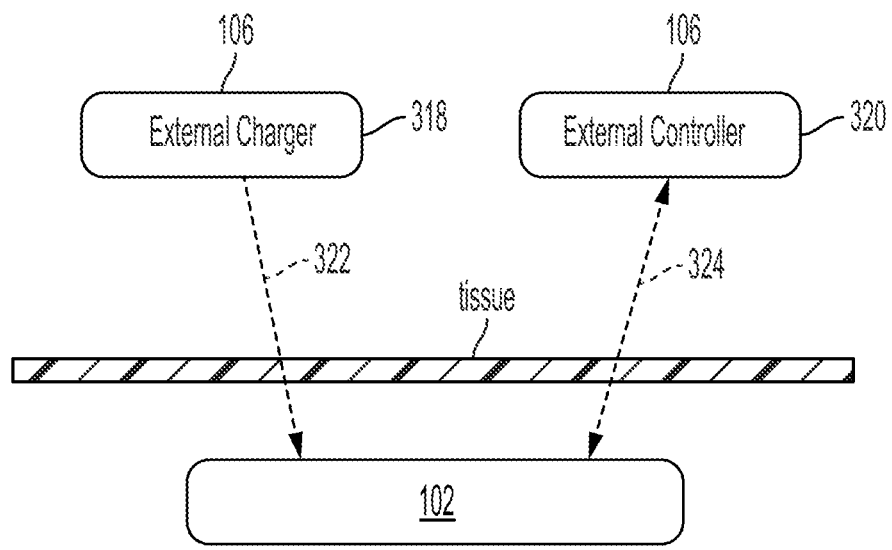
FIG. 3B is a schematic diagram of the IMD of FIG. 3A in operation with a receiving device.

FIG. 3B further shows the external components (for example, the receiving device 106) referenced above, which may be used to communicate with the IMD 102. The receiving device 106 may include an external charger 318 and an external controller 320. The external controller 320 may be used to control and monitor the IMD 102 via a bidirectional wireless communication link 324 passing through a patient's tissue. For example, the external controller 320 may be used to monitor the measurements taken by the electrodes 112 and 114.

Communication on the wireless communication link 324 can occur via magnetic inductive coupling between an antenna (not shown) in the external controller 320 and the antenna 204 in the IMD 102. The magnetic field comprising the link 324 may be modulated via Frequency Shift Keying (FSK) or the like, to encode transmitted data. Other methods including but not limited to short-range RF telemetry (e.g., Bluetooth, WiFi, Zigbee, MICS, etc.) may also be employed.

The external charger 318 provides power to recharge the battery 304 should the battery 304 be rechargeable. Such power transfer may occur by energizing a charging coil (not shown) in the external charger 318, which produces a magnetic field 322 which then energizes the charging coil 306 in the IMD 102, which is rectified, filtered, and used to recharge the battery 304.

Furthermore, the antenna 204 may be positioned to face the tissue, or positioned to be at the location closest to the skin side or the exterior side of the patient's body, in order to minimize or avoid RF interference by having less body tissue to transmit wireless data therethrough. In addition, the integrated circuitry in some examples includes a Kelvin connection to the first electrode 112 and the second electrode 114. In certain instances, the IMD 102 may include an accelerometer to determine whether or not the IMD 102 has turned or flipped. The accelerometer may determine periods of electrode inactivity to determine a stable signal and select between the first electrode 112 and the second electrode 114.

In some examples, the housing 110 may be formed by having two separate housing portions (for example, one defining the frontward facing portion 208 and the other defining the rearward facing portion 210) combined or conjoined together into one component. In some examples, the combined portions may be laser-welded or ultrasonically welded together to form the housing 110. In some examples, the combined portions may be brazed together using any suitable metal such as gold alloys to form the housing 110. In some examples, the combined portions may be attached together using a suitable adhesive to form the housing 110. In some examples, the combined portions may be shrink-wrapped to form the housing 110 using any suitable polymer, including but not limited to PVC, polyolefin, polyethylene, and polypropylene. In some examples, the housing 110 is sealed to ensure hermiticity using any one or more of the methods outlined above.

The functionality of the first electrode 112 and the second electrode 114 may be controlled by the integrated circuitry (e.g., microcontroller 308 and/or ASICs 310). For example, the integrated circuitry may be configured to select between the first electrode 112 and the second electrode 114. In addition, the integrated circuitry may be configured to measure sensing capability of the first electrode 112 and sensing capability of the second electrode 114. In certain instances, the integrated circuitry may be configured to select between the first electrode 112 and the second electrode 114 in response to determining which of the first electrode 112 and the second electrode 114 has a greater of the sensing capability. The integrated circuitry may be configured to measure impedance on a sensed signal of the first electrode 112 and an impedance on a sensed signal of the second electrode 114 to determine the sensing capability of the first electrode 112 and the sensing capability of the second electrode 114. The integrated circuitry being configured to select between the first electrode 112 and the second electrode 114 may increase sensing capabilities and signal capture by selecting whichever of the first electrode 112 and the second electrode 114 has the stronger signal for sensing.

Figure 4:
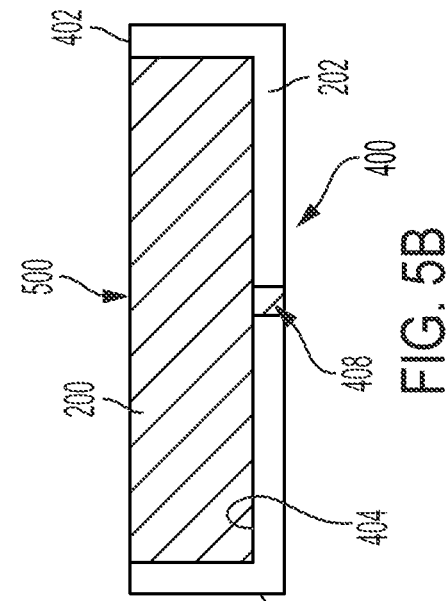
FIG. 4 is a perspective view of a nonconductive body used to contain the electrode of the IMD according to an embodiment.

FIG. 4 shows an example of a nonconductive body 400 used as the nonconductive portion 202 to contain the electrode 112, 114 or the antenna 204 while insulating these components from the housing 110 of the IMD 102, according to some embodiments. Specifically, the nonconductive body 400 has an outer portion defined by a top surface 402 and a side surface 406. The nonconductive body 400 also includes a well 404 that defines a recess relative to the top surface 402. In some examples, the well 404 is approximately 0.01 mm to 0.1 mm, 0.1 mm to 0.5 mm, 0.5 mm to 1 mm, 1 mm to 2 mm, 3 mm to 4 mm, or 4 mm to 5 mm lower than the top surface 402. The well 404 may further include a conduit 408 which is defined as an opening, hole, or aperture that extends through the nonconductive body 400.

Although the nonconductive body 400 is shown as circular in shape when seen from above, it is to be understood that the nonconductive body 400 may be formed in any shape or configuration. For example, the nonconductive body 400 may be formed as an elongated ovular shape according to the nonconductive portion 202 surrounding the antenna 204, as shown in FIG. 2. When the nonconductive body 400 is an elongated ovular shape, it may or may not include a well that defines a recess relative to the top surface 402. In some examples, an outer diameter 410 of the nonconductive body 400 (also referred to as a diameter of the nonconductive portion 202) may be between approximately 1.1 to 1.2 times, 1.2 to 1.5 times, 1.5 to 2 times, 2 to 3 times, or 3 to 5 times greater than an outer diameter 412 of the well 404 (also referred to as a diameter of the conductive portion 200), for example.

Figure 5A:
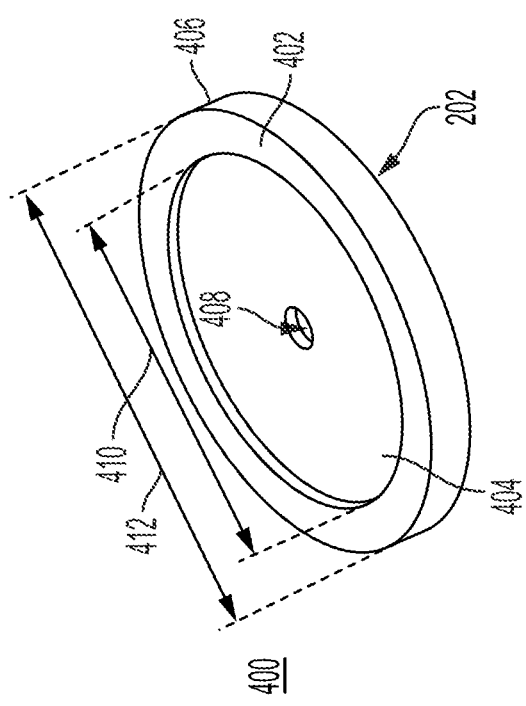
FIG. 5A is a side view of the nonconductive body shown in FIG. 4 with a conductive material deposited therein.

The nonconductive body 400 with the well 404 may be prepared using any insulating material including but not limited to ceramic, glass, or sapphire. The conduit 408 may then brazed with a conductive material such as copper and zinc alloy. In some examples, the housing 110 has an opening into which the nonconductive body 400 may be positioned prior to or after brazing. In embodiments, one end of the wire is brazed to the conduit 408 and the other end of the wire may be connected to the PCB 312. Alternatively, in some examples, the nonconductive body 400 may be brazed directly to the surface 300 of the PCB 312, where the electrical traces may be printed on the surface 300, instead of to the wire. After brazing, a conductive material to form the conductive portion 200 of the electrode, for example titanium nitride (TiN), may be deposited or sputtered into the conduit 408 and the well 404 until a top portion 500 of the conductive material is level with or protrudes past the top surface 402 of the nonconductive body 400 as shown in FIG. 5A.

Figure 5B:
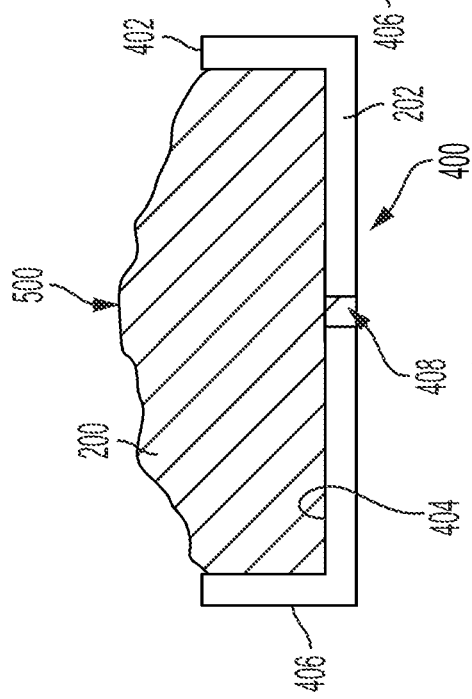
FIG. 5B is a side view of the nonconductive body shown in FIG. 5A after the deposited conductive material is smoothened.

In embodiments, the extraneous portion that extends past the top surface 402 (including the top portion 500) may be smoothened using methods such as laser etching or surface grinding such that the surface of the conductive portion 200 is essentially flush with the top surface 402 of the nonconductive body 400 as shown in FIG. 5B. The term "essentially flush" may indicate that the difference between the two neighboring surfaces is small enough to be essentially undetectable by the naked eye, or if the difference is minuscule so as to not have any effect during the use of the device. In some examples, the difference may be less than approximately 1 mm or 0.5 mm. In some examples, this difference may be less than approximately 0.1 mm or even less than 0.01 mm.

In some examples, the surface grinding may be achieved via back grinding using suitable back-grinding tapes. In some examples, masking processes may be employed in addition, or alternative, the back-grinding method. Alternatively, other methods of depositing the conductive material into the conduit 408 and the well 404 may be employed. In some examples, semiconductor photolithography may be used, which can pattern or define the electrode or conductive region 200 with more precision than some of other methods. If ceramic is used for the nonconductive body 400, the resulting electrode 112, 114 formed using the nonconductive body 400 in FIG. 5B retains physical properties similar to a cermet, for example having high temperature resistance and hardness as well as the ability to undergo plastic deformation without rupturing or fracturing.

Additionally, or alternatively, the antenna 204 and/or the nonconductive body 400 may be made to be essentially flush with the outer surface 206 (i.e., the frontward facing portion 208 or the rearward facing portion 210) of the IMD 102, which allows for a smaller profile for the IMD 102 as compared to having the metal components directly attached to the outer surface 206 of the IMD 102.

The illustrative components shown in the figures are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in the figures may be, in embodiments, integrated with various other components depicted therein (and/or components not illustrated), all of which are considered to be within the ambit of the disclosed subject matter.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A method for forming an electrode on an implantable medical device (IMD), comprising:
   forming a nonconductive body comprising a well having a bottom surface and at least one side surface extending from the bottom surface;
   forming a conduit through the bottom surface;
   inserting the nonconductive body into an opening in an external surface of the IMD;
   depositing conductive material into the well; and
   coupling the conductive material to a circuit of the IMD via the conduit through the bottom surface of the well.

2. The method of claim 1, wherein coupling the conductive material to the circuit of the IMD comprises brazing a wire that couples the conductive material to the circuit.

3. The method of claim 1, wherein depositing conductive material into the well comprises using photolithography and/or vapor deposition techniques.

4. The method of claim 1, wherein the conductive material is titanium nitride (TiN).

5. The method of claim 1, wherein the nonconductive body is made of ceramic, glass, or sapphire.

6. The method of claim 1, wherein the well is approximately 0.1 to 1 millimeters deep.

7. The method of claim 1, wherein an outer diameter of the nonconductive body is between approximately 1.1 to 1.5 times larger a diameter of the bottom surface.

8. The method of claim 1, wherein the nonconductive body is an elongated nonconductive body, the method further comprising:
   depositing the conductive material onto the nonconductive body in a non-linear path;
   wherein the conductive material is coupled to the circuit of the IMD via the conduit through the nonconductive body.

9. The method of claim 8, further comprising surface-grinding or laser etching a top of the nonconductive body, the conductive material, or the nonconductive body and the conductive material to remove excess of the nonconductive body, the conductive material, or the nonconductive body and the conductive material.

10. The method of claim 8, wherein the nonconductive body is made of ceramic, glass, or sapphire.

11. The method of claim 8, wherein the conductive material is titanium nitride (TiN).

12. The method of claim 1, further comprising: brazing the conduit with the conductive material prior to depositing the conductive material into the well.

13. The method of claim 12, wherein coupling the conductive material to the circuit of the IMD comprises directly brazing the nonconductive body to a surface of the circuit on which a plurality of electrical traces are printed.

14. An implantable medical device (IMD), comprising:
   a housing enclosing a power supply, a processing device, and memory;
   a nonconductive body arranged in an opening of the housing, the nonconductive body comprising a well having a bottom surface and at least one side surface extending from the bottom surface;
   a conductive material deposited into the well, wherein the conductive material is electrically coupled to the processing device.

15. The IMD of claim 14, wherein a top surface of the conductive material is flush with a top surface of the housing, wherein a top surface of the conductive material is flush with a top surface of the nonconductive body, or wherein a top surface of the conductive material is flush with the top surface of the housing and the top surface of the nonconductive body.

16. The IMD of claim 14, wherein the nonconductive body is made of ceramic, glass, or sapphire.

17. The IMD of claim 14, wherein the conductive material is titanium nitride (TiN).

18. The IMD of claim 14, wherein the bottom surface of the well includes a conduit which extends through the nonconductive body and is brazed with the conductive material.

19. The IMD of claim 18, wherein the processing device comprises a circuit board having a surface on which a plurality of electrical traces are printed, and the nonconductive body is directly brazed, using the conductive material, to the surface of the circuit board such that the conductive material deposited into the well is electrically coupled with the electrical traces.

* * * * *